United States Patent [19]

Toftness

[11] Patent Number: 4,545,383

[45] Date of Patent: Oct. 8, 1985

[54] ANTENNA STRUCTURE FOR COLLECTION AND DETECTION OF RADIATION

[75] Inventor: Irwing N. Toftness, Cumberland, Wis.

[73] Assignee: Toftness Post-Graduate School of Chiropratic Inc., Cumberland, Wis.

[21] Appl. No.: 496,932

[22] Filed: May 23, 1983

[51] Int. Cl.$^4$ .............................................. A61B 6/00
[52] U.S. Cl. .................................... 128/653; 250/489
[58] Field of Search ........................ 128/653, 632–633; 250/489, 491.1, 526

[56] References Cited

U.S. PATENT DOCUMENTS

| | | | |
|---|---|---|---|
| 3,626,930 | 12/1971 | Toftness | 128/653 |
| 3,629,594 | 12/1971 | Sandberg | 128/653 X |
| 3,831,033 | 8/1974 | Chapa | 250/491.1 |

Primary Examiner—Lee S. Cohen
Assistant Examiner—Angela D. Sykes
Attorney, Agent, or Firm—Leo Gregory

[57] ABSTRACT

A tapered substantially cylindrical housing forming an antenna structure to collect radiation as an emission from a human body and consisting of an antenna, the antenna forming a reflective liner having an upward taper relative to the housing becoming reduced to a small outlet passage in the neck portion of the housing, a sensing plate across the neck portion of the housing above the outlet passage, a shutter pivotal to overlie the outlet passage, a hood having a reflective lining extending upwardly of the housing and providing access to the sensing plate, and both the liner and the hood focus radiation onto the sensing plate.

13 Claims, 8 Drawing Figures

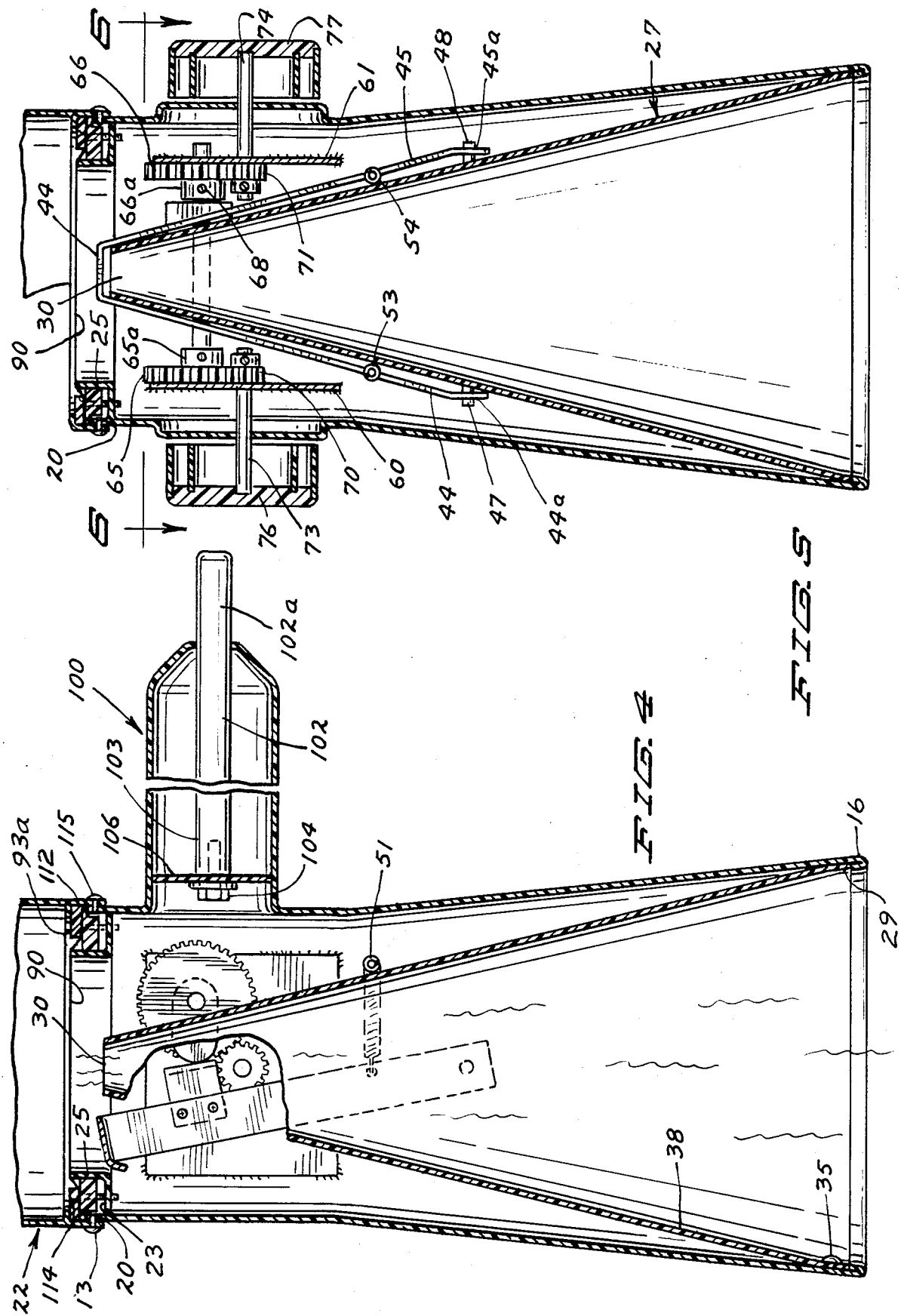

ANTENNA STRUCTURE FOR COLLECTION AND DETECTION OF RADIATION

BACKGROUND OF THE INVENTION

1. Field of Invention

The field of invention relates to a horn type of antenna to collect and focus radiation upon a sensing plate.

2. Description of Previous Art

This invention represents a significant improvement over the prior issued patent to the applicant, U.S. Pat. No. 3,626,930, dated Dec. 14, 1971. Improvement has been attained in the increased perception of radiation collected. This is believed to have been attained by the omission of the lens system disclosed in said patent and in place thereof there is utilized an antenna having a highly reflective interior surface which appears to provide an open window for passage of the radiation collected. There is a clear unimpeded passage through the antenna to the focal area of a sensing plate upon which the radiation is sensed.

SUMMARY OF THE INVENTION

This invention relates to a radiation collecting device to collect radiation emitted from a human body and causing the radiation to be brought to a focus upon a plate member whereon the radiation may be sensed. The human body is known to emit radiation. The intensity of the radiation relates directly to body distress as a function of nerve interference.

The device herein is particularly adapted for use in scanning a spinal column of a human body for detection therein of areas of intensified radiation.

Many complex devices have been utilized to scan the spinal column to detect areas therein indicating nerve interference or nerve impingement. Some such devices as a radiometer are fairly large, not readily handled and require mechanical support.

This invention embodies the use of a hand held readily handled device which collects a relatively wide spherical angle of radiation causing the same to be focused upon a plate member whereon a trained operator by sense of touch may detect and distinguish various intensities of radiation.

This invention is adapted to collect a wide spherical angle of radiation for direct concentration onto a small focal area of a related sensing plate for detection by an operator.

The body emits radiation through a fairly wide band. The device herein is not particularly adapted to collect and focus a specific frequency. The device collects a fairly wide spherical angle of radiation to permit the perception of relative intensities of radiation from various areas of a spinal column and from which the operator determines for correction stressed areas in the body.

It is an object of this invention therefore to provide an antenna structure which is a mechanical hand operated device readily permitting the determination of the location of areas of relative stress within the body of a patient whereby appropriate correction may be applied.

These and other objects and advantages will be set forth in the following description made in connection with the accompanying drawings in which like reference characters refer to similar parts throughout the several views.

BRIEF DESCRIPTION OF THE FIGS.

FIG. 4 is a view in vertical section taken on line 4—4 of FIG. 3 as indicated;

FIG. 5 is a view in vertical section taken on line 5—5 of FIG. 2 as indicated;

DESCRIPTION OF A PREFERRED EMBODIMENT

Figure 1:
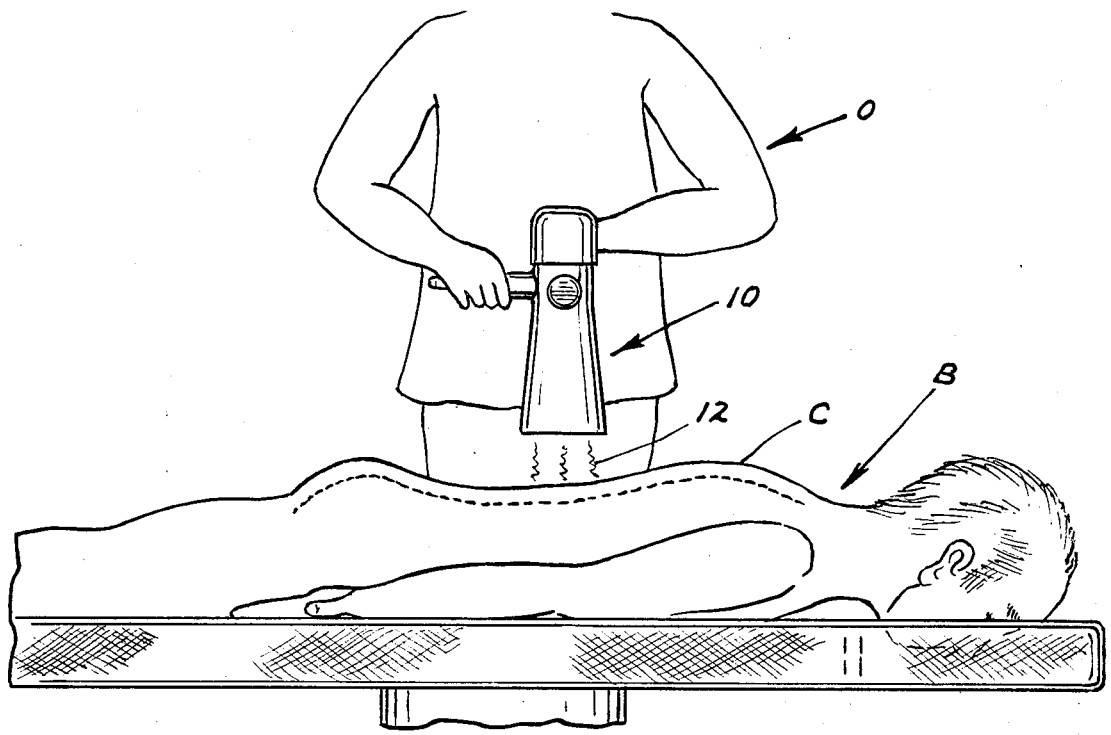
FIG. 1 is a view in rear elevation showing the device herein in operating position.

Referring to the drawings, the radiation collection and detection structure or device comprising the invention herein is indicated generally by the reference numeral 10 and is sometimes referred to herein as an antenna device or an antenna.

In FIG. 1, the reference character 0 indicates an operator holding the device herein in an operating position with regard to the body B of a patient and indicated in said body is spinal column C.

Comprising the antenna device 10 in the embodiment here presented is a housing structure 12 having an outer wall 14 circular in horizontal section and tapering longitudinally from a relatively wide or horn shaped bottom opening 16 to an upper or neck opening 18 of reduced cross sectional width. Said body may be readily formed of a suitable metal and have applied thereto an appropriate exterior coating.

Upstanding from and mounted upon the upper end portion 20 of said housing is a hood 22 which will be described later in some detail.

For purpose of illustration only and not for limitation, a convenient size of said housing for handling purposes is on the order of 10 inches in height, having a bottom diameter on the order of 5–6 inches tapering to a diameter on the order of 4 inches. The cylindrical neck portion 18 is on the order of 3 inches in length.

The upper end portion 20 of said housing (FIGS. 4, 5, 7) is formed having an inwardly extending groove 23 terminating in a central upstanding circular collar or vertical flange 25.

To describe the interior of said housing 12, disposed therein is a reflective cone shaped antenna member 27 having a side wall 28 having a uniform taper therein forming an upper end outlet passage 30 which preferably may be on the order of ¾ inches in diameter.

Said upper end outlet 30 will terminate to be spaced below the focal or central area of a sensing plate 90 to be further described.

Said cone 27 has a bottom 29 corresponding in diameter to the inner bottom 16 of said housing 12 and is suitably fastened by a screw 35 which threads into the wall of said housing as indicated. The cone is preferably made to be seamless. It has been found that said cone may be very suitably made of copper sheet material having its interior surface coated with a gold plating as indicated by the reference numeral 38.

It has been found that a copper surface plated with gold provides an excellent reflective surface for purposes herein.

Figure 6:
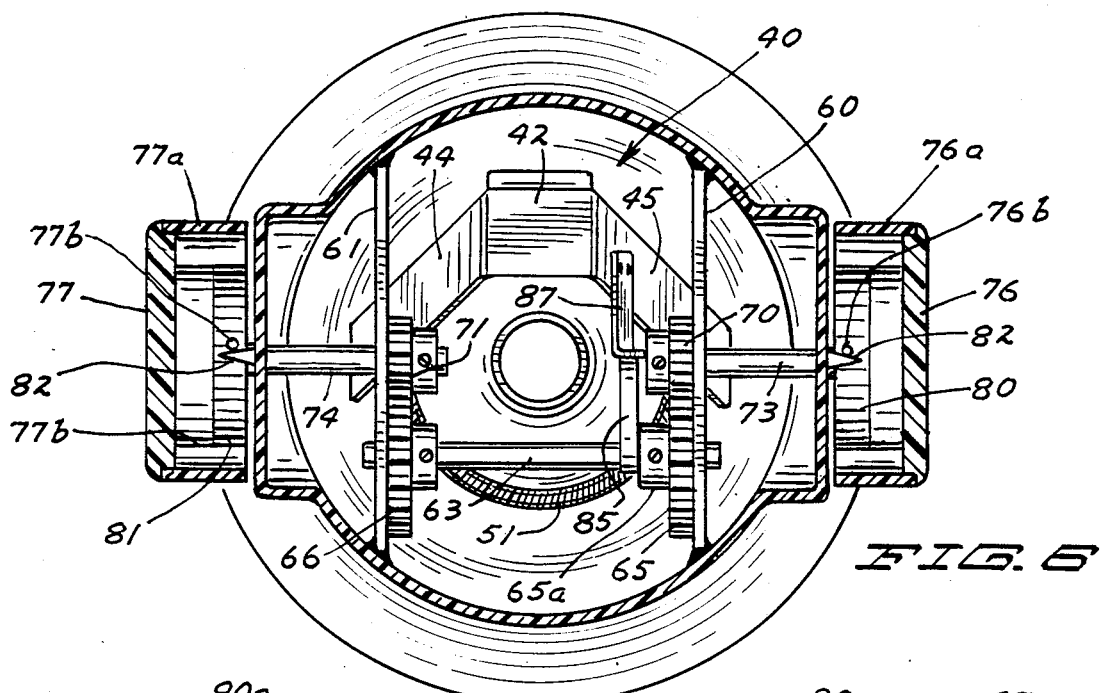
FIG. 6 is a view in horizontal section taken on line 6—6 of FIG. 5.

Arranged to removably overlie said outlet passage 30 is a closure or shutter structure 40 (FIG. 6) which is not unlike a focal plane shutter in a camera lens system.

Said shutter has a top wall 42 and depending leg members 44 and 45 which are flared to correspond to the taper of said antenna member 27. Secured to a pair of opposite sides of said reflective member as by welding and projecting therefrom are a pair of projecting pivots 47 and 48 which pivotally engage the lower portions of said leg members 44 and 45 by extending through accommodating holes 44a and 45a therein.

Extending partially about said antenna member 27 is a coil spring 51 suitably secured through apertures of said leg portions 44 and 45 as at 53 and 54, said spring normally urges said shutter in position to have the end wall 44 thereof overlie said outlet passage 30.

To move said shutter to its non-operative position to uncover said outlet passage 30, the following structure is described.

At the inner portion of said neck 18 at opposed sides thereof, a pair of plate members 60 and 61 are suitably secured. Mounted between said plate members and journaled therein at the side of said antenna 27 as said coil spring 51 is a shaft 63 having toothed gears 65 and 66 respectively mounted thereon at the inner or facing sides of said plate members, said toothed gears having hub portions 65a and 66a, being secured to said shaft 63 by set screws 68.

Also mounted onto said plate members 60 and 61 are spur gears 70 and 71 respectively carried on shafts 73 and 74 which extend oppositely through said housing 12 to have secured thereto outwardly thereof cylindrical control knobs 76 and 77. Said knobs each have corresponding cylinders of indicia 80 and 81 therein indicating numerical increments of measure, said indicia to be read in connection with the stationary indicators 82 which suitably project from the adjacent portion of the housing. Said knobs have transparent edge portions 76a and 77a through which the indicia is read. Said knobs respectively have stop pins 76b and 77b.

Mounted suitably on said shaft 63 and adjacent the hub 65a of said gear 65 is a cam 85.

Suitably secured as by a weld or a metal screw onto said shutter leg 45 in operative relation with said cam 85 is a cam follower 87. Thus the rotation of said knobs 76 and 77 in an appropriate direction cause said cam 85 to move said cam follower 87 and the shutter 40 therewith to a nonoperative position uncovering the outlet passage 30. When said cam is moved in a direction to be out of engagement with said cam follower, said spring 51 normally urges said shutter into operative position having its top or end wall 44 overlie said outlet passage 30.

Figure 7:
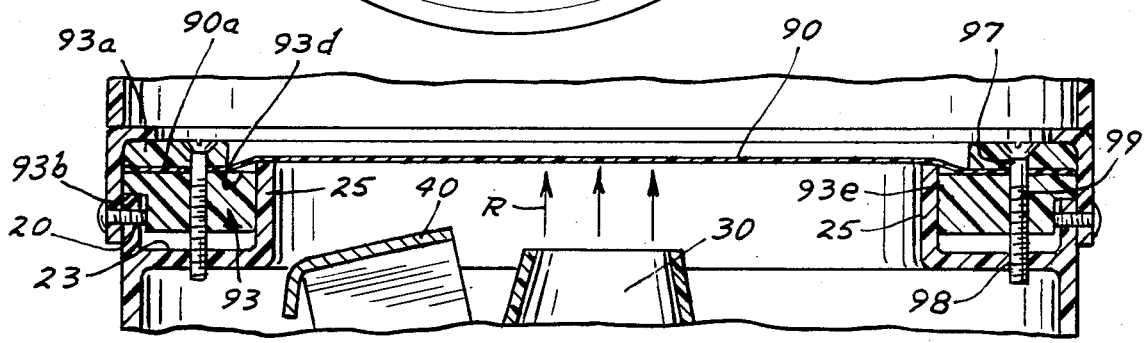
FIG. 7 is a fragmentary view in vertical section showing a detail of structure.
Figure 8:
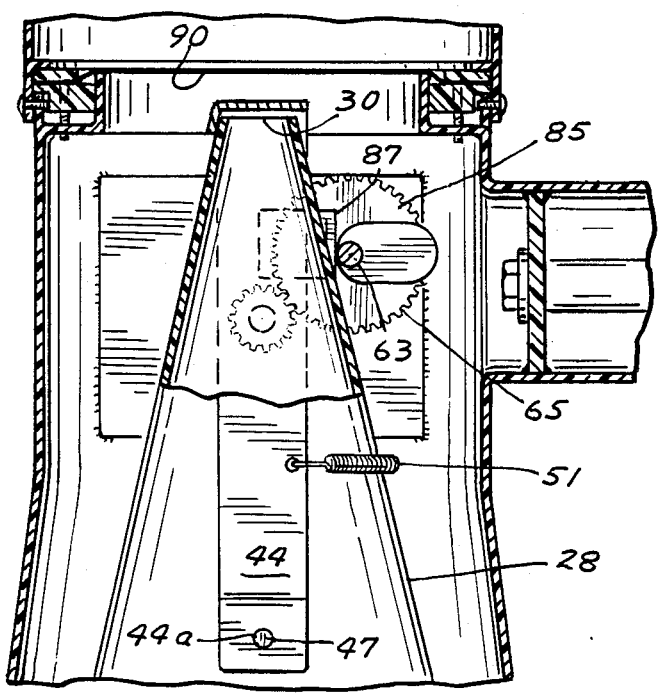
FIG. 8 is a broken view in vertical section showing details of structure.

The sensing plate 90 has been found to be very suitably formed of a teflon sheet material having a thickness on the order of 0.002 to 0.004 inches and is regarded as a clear window for the passage of radiation therethrough. Radiation R as indicated in FIG. 7 is clearly tangibly sensed by touch of the operator upon said plate.

Said sensing plate as here presented is indicated as having a thickness of 0.002 inches. Said plate is secured by being embedded about its periphery as at 90a into a ring 93 formed as of a suitable plastic material. Said ring is offset or stepped in vertical section with the upper ring portion 93a extending outwardly as at 93b to form a peripheral flange. In like manner, said lower ring 93 has an inner peripheral portion 93d extending inwardly of said upper ring portion 93a.

Said ring 93 has its bore or central opening 93e of a diameter to fit nicely about said vertcal flange 25, said flange bearing directly upwardly against said sensing plate 90. Spaced about said upper ring portion 93a and therethrough are apertures 97 and in alignment therewith are corresponding holes 98 tapped into said groove 23 to receive screws 99.

Said ring 93 seated upon said collar or flange 25 is supported thereon spaced from said groove therebelow whereby said screws 99 in being threaded into said holes 98 draw said ring member downwardly against the upper edge of said flange 25 to tighten or place said sensing plate 90 under whatever degree of tension may be found to be desirable.

Formed integrally with said housing 12 is a projecting cylindrical handle 100 having a rod 102 of a substantially small diameter extending therethrough and outwardly thereof, said rod being seen to have a nut 104 threaded onto a reduced end of its inner end portion 103 and said nut bears against a plate member 106 which forms a wall at the inner end portion of said handle 100, all of which is illustrated in FIG. 4. Said rod 102 may be used to hold said housing in a hanging position when not in use by merely having its projecting end portion 102a disposed into an accommodating aperture of a suitable vertical support member not here shown.

Figure 2:
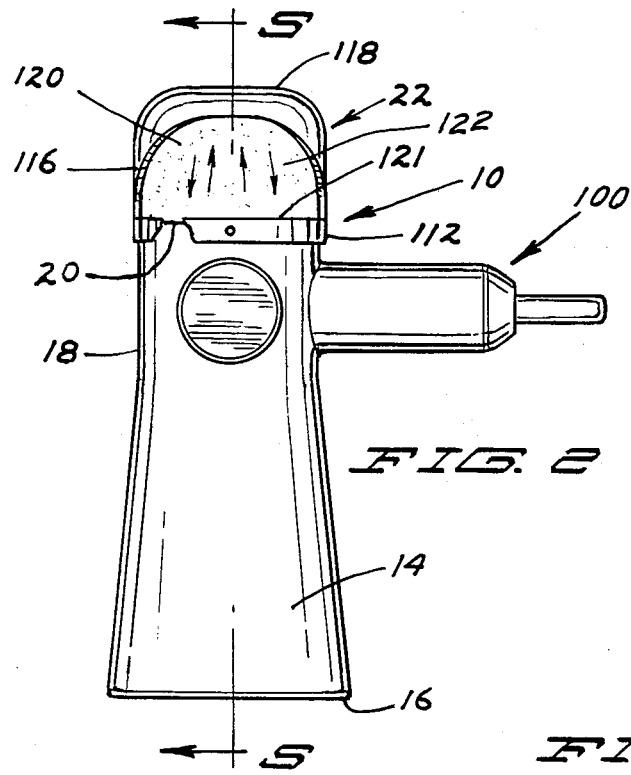
FIG. 2 is a view in front elevation.
Figure 3:
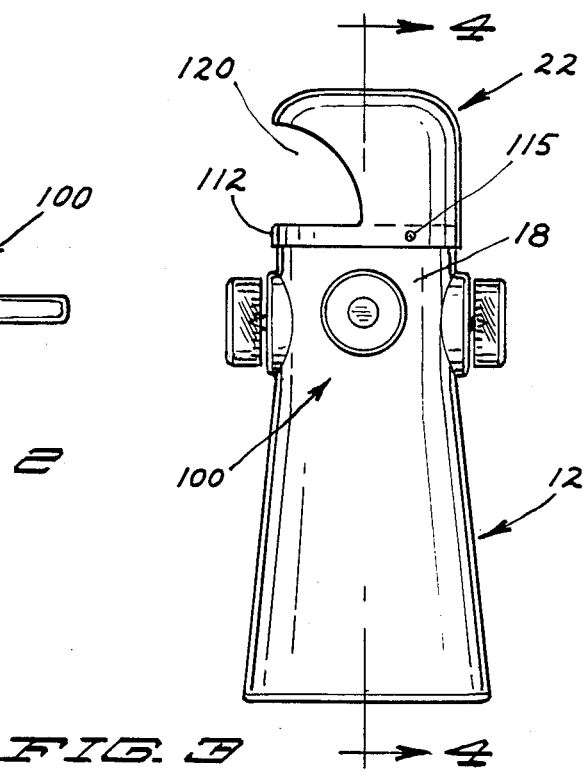
FIG. 3 is a view in side elevation.

Referring now to said hood 22 (FIGS. 2 and 3), the base of said hood is formed as a vertical walled ring 112 having at its upper edge an inward peripheral flange 114, said flange seats upon the upper edge or rim 20 of said housing.

A plurality of set screws 115 are spaced about said ring, said screws extending to underlie the flange 93b (FIG. 7).

Extending upwardly of said ring 112 is a cylindrical side wall 116 terminating in a domed upper or top wall 118. Said side wall has an upwardly tapered opening 120 therein which at its bottom 121 extends approximately half the circumference of said ring 112—said space 120 taken being sufficient to provide hand access to said sensing plate.

Said hood is provided with a gold plate interior reflective surface 122 in the manner of the reflective surface of said member 27. The curvature of said top wall is such that the radiation deflected therefrom tends to focus upon the central or focal area of said sensing plate 90.

OPERATION

The customary manner in which the spinal column of a patient is examined and the findings thereof analyzed by a practitioner is by direct sense of touch characterized as palpation. It is known that the body generally and that for purposes herein, the spinal column emits radiation and that increase in the intensity of radiation emitted in specific areas thereof in excess of what could be regarded as a normal level of radiation is a direct result of and a function of a distress condition in the nerve system of the body or nerve interference as evidenced in the spinal column. A symptom of distress detected by examination of the spinal column does not necessarily indicate that a nerve interference condition is in the spinal column. The condition of distress may be elsewhere and it is the experienced skill of the practitioner which enables him to make an analysis and locate the distress.

The device 10 herein is very suitably used as an auxiliary analytic device which supplements the findings derived from palpation and other means of examination.

For optimum results, with the patient prone upon an examination table, the device is held preferably in a position from being just clear of the surface of the patient's body to a height on the order of four to six inches thereabove. The device is moved to scan the spinal column for detection of the areas from which relatively greater intensities of radiation are detected. The bone structure of the spinal column attenuates very little the passage of radiation therethrough.

The open end bottom portion 16 is of a width that at the elevation indicated a wide spherical angle of radiation is collected and passed upwardly through the outlet passage 30 to have a concentration thereof focused upon the sensing plate 90.

A very light application of a dusting powder placed upon said sensing plate provides for a smooth free passage of fingertips upon the sensing plate.

The spinal column may be scanned several times with the fingertips of the operator moving over the focal area of the sensing plate to assure that the relatively greater intensity of radiation sensed in one or more places is sensed in the same places.

Appropriate correction is applied to the body of the patient and when the correction has been completed, the spinal column is scanned again with said device to determine if the level of intensity of radiation detected is fairly uniform, then in the opinion of the practitioner the correction has been adequate.

Thus, there is no need to consult with the patient as to the presence or location of distress with regard to the nerve system. This is a purely objective analysis.

The shutter 40 provides means to shut off to whatever extent may be desirable the passage of radiation through the outlet 30 whereby relative intensities of radiation present are readily detected and a distinction may be readily achieved between the absence of radiation and the presence of a low level of radiation.

Analyses achieved by means of the device herein has been verified by independent like examinations with an electronic radiometer which is wholly electronically objective and which has confirmed the accuracy of analyses achieved with the device herein.

It will of course be understood that various changes may be made in form, details, arrangement and proportions of the parts without departing from the scope of the invention herein which, generally stated, consists in an apparatus capable of carrying out the objects above set forth, in the parts and combinations of parts disclosed and defined in the appended claims.

What is claimed is:

1. A hand held mechanical antenna structure collecting radiation for detection, having in combination
   an elongated housing having open upper and lower ends,
   a cone shaped antenna member disposed within said housing,
   an outlet of relatively small width at one end of said antenna member,
   a sensing plate member carried by said housing spaced above said outlet,
   a shutter member in operative association with said outlet,
   means carried by said housing for moving said shutter member relative to said outlet,
   a hood member upstanding from the upper end of said housing overlying said sensing plate member, and
   an opening in said hood member providing access to said sensing plate member.

2. The structure of claim 1, wherein
   said housing is substantially cylindrical in form.

3. The structure of claim 1, wherein
   said antenna member has an open bottom fitting into said open lower end of said housing.

4. The structure of claim 1, including
   a collar upstanding from the upper end of said housing, and
   said sensing plate member being supported upon said collar.

5. The structure of claims 1 or 4, including
   means carried by said housing for adjusting the tension of said sensing plate member.

6. A hand held mechanical antenna structure collecting radiation for detection, having in combination
   an elongated open ended housing,
   an annular collar upstanding from an upper end portion of said housing,
   a sensing plate member seated upon said collar,
   a dome shaped hood supported by said housing disposed over said sensing plate member,
   an opening in said hood for access to said sensing plate member,
   an antenna member within said housing having its wall tapering upwardly to an outlet, said outlet being centered below said sensing plate member,
   said antenna member collecting a wide spherical angle of radiation passing the same onto said sensing plate member,
   a shutter member mounted in said housing disposed to overlie said outlet,
   means carried by said housing for operating said shutter member moving the same to uncover said outlet,
   means in association with said last mentioned means for normally urging said shutter member to overlie said outlet, and
   carrying means attached to said housing.

7. The structure of claim 2, wherein
   said sensing plate member comprises
   a ring member having a periphery fitting about said annular collar,
   a flexible sheet material forming a sensing plate,
   the periphery of said sensing plate being embedded within said periphery of said ring member,
   an annular groove within said upper end portion of said housing underlying said ring member, and
   means carried by said housing drawing said ring member into said groove for adjusting the tension of said sensing plate member upon said collar.

8. The structure of claim 6, wherein
   said antenna member is formed of a copper sheet material, and
   a gold plating ring forms an inner reflective surface of said antenna member.

9. The structure of claim 2, wherein
   said shutter member comprises an end wall overlying said outlet,
   a pair of diverging legs depend from said end wall along the wall of said antenna member in opposed relation, and
   means carried by said antenna member for pivotally securing adjacent lower end portions of said legs.

10. The structure of claim 2, wherein said shutter member comprises an end wall overlying said outlet, a pair of diverging legs depend from said end wall in opposed relation overlying said wall of said antenna member, means carried by said antenna member pivotally securing adjacent lower end portions of said legs, and means carried by said antenna member engaging said legs and normally urging said end wall to overlie said outlet.

11. The structure of claim 2, wherein said shutter member comprises an end wall overlying said outlet, a pair of legs in opposed relation extend from said end wall along said antenna member, means carried by said antenna member for pivotally securing said legs, said shutter member operating means comprising a gear train within said housing, a shaft in connection with said gear train, means exterior of said housing carried by said shaft for operating said shaft, a cam carried by said shaft within said housing, and a cam follower carried by one of said legs engaged by said cam moving said shutter member in a direction away from said outlet.

12. The structure of claim 2, wherein said shutter member operating means includes means particularly for moving said shutter member in specific increments relative to said outlet.

13. The structure of claim 2, wherein said shutter member operating means includes indicia, said indicia representing increments of movement of said shutter member, and a member manually movable to position said shutter member relative to said outlet.

* * * * *